United States Patent
Han et al.

(10) Patent No.: US 7,335,752 B2
(45) Date of Patent: Feb. 26, 2008

(54) AZOBENZENE DERIVATIVE COMPOUND, PARTICLE AND METHOD OF FABRICATING THE SAME

(75) Inventors: Mina Han, Wako (JP); Masahiko Hara, Wako (JP)

(73) Assignee: Riken, Wako-Shi (JP)

( * ) Notice: Subject to any disclaimer, the term of this patent is extended or adjusted under 35 U.S.C. 154(b) by 22 days.

(21) Appl. No.: 11/269,707

(22) Filed: Nov. 9, 2005

(65) Prior Publication Data

US 2006/0194771 A1 Aug. 31, 2006

(30) Foreign Application Priority Data

Nov. 12, 2004 (JP) .............................. 2004-328963
Dec. 20, 2004 (JP) .............................. 2004-366950

(51) Int. Cl.
*C07C 323/12* (2006.01)

(52) U.S. Cl. ...................... 534/843; 534/851; 534/859; 977/788; 977/901

(58) Field of Classification Search ................ 534/843, 534/851, 859; 977/788, 901
See application file for complete search history.

(56) References Cited

U.S. PATENT DOCUMENTS

| | | | | |
|---|---|---|---|---|
| 3,893,994 A | * | 7/1975 | Steinstrasser ............... | 534/577 |
| 4,395,350 A | * | 7/1983 | Boller et al. .............. | 252/299.1 |
| 6,177,216 B1 | * | 1/2001 | Broer et al. .................. | 430/7 |
| 6,645,771 B1 | * | 11/2003 | Miller et al. ................. | 436/116 |

OTHER PUBLICATIONS

Sano et al., Langmuir, 8, 320-323, 1992.*
Galewski et al., Polish J. Chem., 73, 1357-1371, 1999.*
Zienkiewicz et al., Polish J. Chem., 76, 359-366, 2002.*
Imrie et al., Macromolecules, 26, 545-550, 1993.*
Akiyama et al., J. Phys. Chem. B, 107, 130-135, 2003.*

* cited by examiner

*Primary Examiner*—Fiona T Powers
(74) *Attorney, Agent, or Firm*—Birch, Stewart, Kolasch & Birch, LLP (57) ABSTRACT

An azobenzene derivative compound denoted by general formula (I):

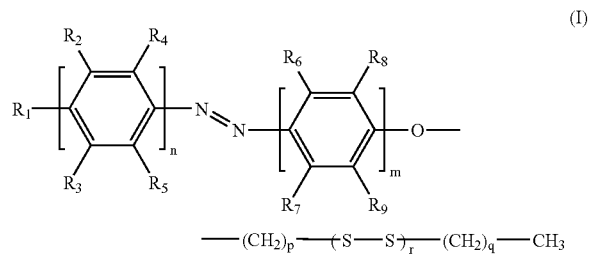

(wherein $R_1$ denotes a hydrogen atom, halogen atom, cyano group, amino group, ester group, nitro group, alkyl group, alkoxyl group, cycloalkyl group, or heterocyclic group; m and n each independently denote an integer ranging from 1 to 6; $R_2$ to $R_9$ each independently denote a hydrogen atom or alkyl group; p and q each independently denote an integer ranging from 3 to 28; and r denotes 0 or 1). Particles formed by aggregates of the above azobenzene derivative compounds and method of fabricating the same.

15 Claims, 7 Drawing Sheets

Fig. 1

(c) 390 minutes after UV light irradiation (b) 180 minutes after UV light irradiation (a) 120 minutes after UV light irradiation

1 = 2 × 10⁻⁶ M (excited at 325 nm),
2 = 4 × 10⁻⁵ M (excited at 325 nm),
3 = 2 × 10⁻⁴ M (excited at 325 nm),
4 = 8 × 10⁻⁴ M (excited at 325 nm),
5 = 2 × 10⁻³ M (excited at 440 nm)

AZOBENZENE DERIVATIVE COMPOUND, PARTICLE AND METHOD OF FABRICATING THE SAME

CROSS-REFERENCE TO RELATED APPLICATIONS

The present application claims priority under 35 U.S.C. §119 to Japanese Patent Application No. 2004-328963 filed on Nov. 12, 2004 and Japanese Patent Application No. 2004-366950 filed on Dec. 20, 2004.

BACKGROUND OF THE INVENTION

1. Field of the Invention

The present invention relates to novel azobenzene derivative compounds, particles formed by aggregates of said azobenzene derivative compounds and method of fabricating the same.

2. Discussion of the Background

Azobenzene is known not to be emissive at room temperature. Accordingly, it has been proposed that metals or emissive substances be introduced into azobenzene to obtain emissive azobenzene derivatives (Yutaka, T.; Mori, I.; Kurihara, M.; Mizutani, J.; Tamai, N.; Kawai, T.; Irie, M.; Nishihara, H. Inorg. Chem. 2002, 41, 7143., Aiello, I.; Ghedini, M.; Deda, M. D. J. Lumin. 2002, 96, 249. Ghedini, M.; Pucci, D.; Calogero, G.; Barigelletti, F. Chem. Phys. Lett. 1997, 267, 341. Nihei, M.; Kurihara, M.; Mizutani, J.; Nishihara, H. J. Am. Chem. Soc. 2003, 125, 2964. Tsuchiya, S. J. Am. Chem. Soc. 1999, 121, 48.). However, these azobenzene derivatives have problems in the form of shifted absorption bands or reduced isomerization rates.

On the other hand, it has been reported that when a compound exhibiting weak fluorescence was added to a mixed solvent of water and an organic solvent to form aggregates (for example, nanometer-scale aggregates (nanoparticles)), an emission enhancement of several hundred times that which was present prior to aggregation was exhibited.

Generally, aggregates such as nanoparticles are formed by adding an amphiphilic substance having a hydrophilic moiety and a hydrophobic moiety to a mixed solvent of water and an organic solvent. However, amphiphilic substances have problems in that they are difficult both to synthesize and to purify.

SUMMARY OF THE INVENTION

Accordingly, it is an objective of the present invention to provide novel azobenzene derivatives that are readily synthesized and purified, and permit the simple and ready formation of aggregates.

Means for solving the aforementioned objective are as follows:

[1] An azobenzene derivative compound denoted by general formula (I):

$$—(CH_2)_p—(S—S)_r—(CH_2)_q—CH_3$$

(wherein $R_1$ denotes a hydrogen atom, halogen atom, cyano group, amino group, ester group, nitro group, alkyl group, alkoxyl group, cycloalkyl group, or heterocyclic group; m and n each independently denote an integer ranging from 1 to 6; $R_2$ to $R_9$ each independently denote a hydrogen atom or alkyl group; p and q each independently denote an integer ranging from 3 to 28; and r denotes 0 or 1).

[2] The azobenzene derivative compound according to [1], wherein, in general formula (I), $R_1$ denotes a cyano group, nitro group, hydrogen atom, alkoxyl group, ester group, or alkyl group having 1 to 8 carbon atoms.

[3] The azobenzene derivative compound according to [1], wherein, in general formula (I), $R_1$ denotes an alkyl group, heterocyclic group, or halogen atom.

[4] The azobenzene derivative compound according to [1], wherein, in general formula (I), $R_2$ to $R_9$ all denote a hydrogen atom.

[5] The azobenzene derivative compound according to [1], wherein, in general formula (I), n denotes an integer ranging from 2 to 6.

[6] The azobenzene derivative compound according to [1], wherein, in general formula (I), m is 1 or 2.

[7] The azobenzene derivative compound according to [1], wherein, in general formula (I), p and q each independently denote an integer ranging from 3 to 22.

[8] The azobenzene derivative compound according to [1], wherein, in general formula (I), r is 0.

[9] Particles formed by aggregates of the azobenzene derivative compounds according to any of [1] to [8].

[10] The particles according to [9], wherein the particle has a diameter ranging from 10 nm to 10 μm.

[11] A method of fabricating the particles according to [9], wherein UV light is irradiated to an organic solvent containing the azobenzene derivative compound according to any of [1] to [8] to form aggregates of said azobenzene derivative compounds.

[12] The method according to [11], wherein concentration of said azobenzene derivative compound in the organic solvent ranges from $10^{-7}$ to $10^{-3}$ M.

[13] The method according to [11], wherein concentration of said azobenzene derivative compound in the organic solvent ranges from $10^{-6}$ to $10^{-4}$ M.

[14] A method of fabricating the particles according to [10], wherein UV light is irradiated to an organic solvent containing the azobenzene derivative compound according to any of [1] to [8] to form an aggregate of said azobenzene derivative compound.

[15] The method according to [14], wherein concentration of said azobenzene derivative compound in the organic solvent ranges from $10^{-7}$ to $10^{-3}$ M.

[16] The method according to [14], wherein concentration of said azobenzene derivative compound in the organic solvent ranges from $10^{-6}$ to $10^{-4}$ M.

Based on the azobenzene derivative compound of the present invention, it is possible to form particles formed by aggregates simply by irradiation with UV light.

Further, the azobenzene derivative compound of the present invention achieves marked light-emission amplification through the formation of aggregates.

DESCRIPTION OF THE EMBODIMENTS

The present invention will be described in detail below.

[Azobenzene Derivative Compound]

The azobenzene derivative compound of the present invention is the azobenzene derivative compound denoted by general formula (I):

(wherein $R_1$ denotes a hydrogen atom, halogen atom, cyano group, amino group, ester group, nitro group, alkyl group, alkoxyl group, cycloalkyl group, or heterocyclic group; m and n each independently denote an integer ranging from 1 to 6; $R_2$ to $R_9$ each independently denote a hydrogen atom or alkyl group; p and q each independently denote an integer ranging from 3 to 28; and r denotes 0 or 1).

$R_1$ denotes a hydrogen atom, halogen atom, cyano group, amino group, ester group, nitro group, alkyl group, alkoxyl group, cycloalkyl group, or heterocyclic group. Examples of halogen atoms are fluorine, chlorine, and iodine. Examples of ester groups are R'OCO— groups (where R' denotes an alkyl group); for example, R' may be a methyl group or an ethyl group. The alkyl group may be a linear or branched alkyl group having 1 to 8 carbon atoms, for example. The alkoxyl group may be an alkoxyl group having 1 to 8 carbon atoms; specifically, it may be a $CH_3O$— group, $CH_3CH_2O$— group, or the like. Further, the cycloalkyl group may be a cycloalkyl group having six carbon atoms, for example. Examples of heterocyclic groups are heterocyclic groups containing nitrogen atoms (such as a pyridyl group).

Considering the availability of starting materials, $R_1$ is desirably a cyano group, nitro group, hydrogen atom, alkoxyl group, ester group, alkyl group having 1 to 8 carbon atoms. Further, from the perspective of the isomerization rate of the azobenzene derivative compound, $R_1$ is desirably an alkyl group, heterocyclic group, or halogen atom.

In general formula (I), m and n each independently denote an integer ranging from 1 to 6. From the perspectives of the availability of starting materials and particle (aggregate) formation, n is desirably equal to or greater than 2 and m is desirably 1 or 2.

$R_2$ to $R_9$ each independently denote a hydrogen atom or alkyl group. The alkyl group may be a linear or branched alkyl group having 1 to 4 carbon atoms. Considering the availability of starting materials, $R_2$ to $R_9$ are desirably hydrogen atoms. When m and n denote integers of equal to or greater than 2 in general formula (I), the substituents of the phenylene group in the repeating unit may be identical or different.

In general formula (I), p and q each independently denote an integer ranging from 3 to 28. Considering the availability of starting materials and the like, p and q desirably each independently denote an integer ranging from 3 to 22.

In general formula (I), r denotes 0 or 1. Since the azobenzene derivative compound of the present invention in which r denotes 1 has an S—S bond within the molecule, it can be immobilized on a gold substrate by utilizing a gold-thiol bond. From the perspective of ease of synthesis, r is desirably 0.

Specific examples of the azobenzene derivative compound of the present invention are shown below.

-continued

(In the above formulas, X denotes a halogen atom; R denotes an alkyl group; and p, q, and r and defined as above.)

The azobenzene derivative compound of the present invention can be synthesized by a known method. For example, the starting compound denoted by general formula (II) and the starting compound denoted by general formula (III) can be diazo-coupled to obtain the hydroxyazobenzene derivative denoted by general formula (IV).

Next, an alkyl chain can be introduced by a known method into the hydroxyazobenzene derivative (IV) that has been obtained to obtain an azobenzene derivative compound (V) in which r denotes 0 in general formula (I).

An azobenzene derivative compound in which r denotes 1 in general formula (I) can be obtained by introducing a dibromoalkane, for example, into above-described hydroxyazobenzene derivative (IV); reacting the compound obtained with sodium thiosulfate to obtain a Bunte salt; and reacting the Bunte salt with an alkyl thiolate. Reference can be made to Japanese Unexamined Patent Publication (KOKAI) No. 2002-20368 with respect to the synthesis method. However, the method of synthesizing the azobenzene derivative compound of the present invention is not limited to the above-cited methods. Known methods such as column chromatography may also be employed as a purification method to obtain the azobenzene derivative compound of the present invention. The verification of the product obtained may be carried out by NMR, IR, Mass (mass analysis), elemental analysis, and other known methods.

[Particles and Method of Fabricating the Same]

The particles of the present invention are formed by aggregates of the azobenzene derivatives of the present invention. In the present invention, the term "aggregate" refers to an aggregation formed by association through self-assembly of the azobenzene derivative compounds of the present invention. The particles of the present invention can be fabricated by irradiating an organic solvent containing the azobenzene derivative compound of the present invention with UV light to form aggregates of the azobenzene derivative compounds. When selecting a solvent, it is desirable to consider whether it is a good solvent to the azobenzene derivative compound used to form the particles, whether the particles formed will be stable and not decompose under extended exposure to light, whether the absorption wavelength of the azobenzene derivative compound employed does not overlap that of the solvent, and the like. Examples of such solvents are dichloromethane, toluene, THF, and DMF.

The concentration of the azobenzene derivative compound in the solvent can be suitably set. It can be from $10^{-7}$ to $10^{-3}$ M, preferably $10^{-6}$ to $10^{-4}$ M.

To obtain the particles of the present invention, UV light is irradiated to an organic solvent containing the azobenzene derivative compound of the present invention. The UV light employed may be those commonly employed (for example, with a wavelength of 230-400 nm), such as UV light with a wavelength of 365 nm or 366 nm.

Azobenzene comes in cis and trans forms; the trans form is the more thermally stable of the two. It is known that when a trans form is irradiated with UV light, it isomerizes into a cis form, which, if placed in a dark location at room temperature, will revert back to the trans form. When the azobenzene derivative compound of the present invention is irradiated for several minutes, for example, with UV light, it undergoes isomerization from the trans form to the cis form. If continuously irradiated with UV light even after having isomerized from the trans form to the cis form, the azobenzene derivative compounds of the present invention aggregate through self-assembly into aggregates (particles). When irradiation with UV light is stopped after the formation of aggregates and the aggregates are stored in a dark location at room temperature, isomerization from the cis to the trans form occurs, but the aggregates (particles) are maintained without dissociation. Thus, in the present invention, the period of irradiation with UV light to form particles is made suitably longer than the period required for isomerization from the trans to the cis form. For example, it may be from 3 minutes to 10 hours, preferably from 6 to 7 hours.

The particles of the present invention may be a spherical particle, for example. The particle diameter may be from 10 nm to 10 μm, for example. The lower the concentration of the azobenzene derivative compound, the smaller the diameter of the particles formed tends to be. The higher the concentration thereof, the larger the diameter of the particles formed tends to be. In the present invention, the concentration of the azobenzene derivative compound may be adjusted to obtain particles of desired particle diameter, ranging from the nanometer to the micrometer level, for example. It is possible to obtain nanometer particles (nanoparticles), for example. In the present invention, the diameter of the particles can be determined from images obtained with scanning electron microscopy (SEM) and transmission electron microscopy (TEM).

The azobenzene derivative compound of the present invention are very weakly emissive prior to aggregation, but after aggregation into aggregates (particles), exhibits fluorescence of an intensity much greater than prior to aggregation. Following irradiation with UV light, the intensity of emission can be further enhanced by placement in a dark location at room temperature.

EXAMPLES

The present invention will be further described below through Examples. However, the present invention is not limited to the modes indicated in Examples.

Example 1

Synthesis of the Azobenzene Derivative Compound $NaNO_2$ (1.24 g) was dissolved in 18 mL of water; a 0 to 5° C. mixed solution of 4-amino-4'cyanobiphenyl (3 g), HCl (6 mL), and water (30 mL) was slowly added dropwise; and the solution was stirred for 30 minutes. A mixed solution of phenol (1.69 g), NaOH (0.78 g), $Na_2CO_3$ (2.06 g), and water was added to the solution, which was then stirred for four hours. The insoluble matter was filtered out, washed three times with water, and vacuum dried, yielding 3.7 g of solid (1).

$^1$H NMR (270 MHz, $CDCl_3$) δ 7.03 (d, 2H, Ar—H), 7.7-8.0 (m, 10H, Ar—H).

A mixed solution of $K_2CO_3$ (3.47 g), tetrabutylammoniumbromide (catalytic quantity), 1,12-dibromododecane (13.7 g), and acetone (200 mL) was stirred for 30 minutes at 60° C. in a $N_2$ atmosphere. To this mixed solution, an acetone solution of the compound (1, 2.5 g) was gradually added dropwise and the mixture was stirred for 11 hours at 60° C. The acetone was removed, the solution was washed three times with water, and the solution was recrystallized from ethyl acetate, yielding 2 g of product (2).

$^1$H NMR (270 MHz, $CDCl_3$) δ1.2-1.6 (m, 16H, $CH_2$), 1.80-1.88 (m, 4H, $BrCH_2CH_2CH_2$, $ArOCH_2CH_2$), 3.40 (t, 2H, $BrCH_2$), 4.05 (t, 2H, $ArOCH_2$), 7.00 (d, 2H, J=8.91 Hz, Ar—H), 7.7-8.0 (m, 10H, Ar—H).

Sodium thiosulfate pentahydrate (0.65 g) was dissolved in 5 mL of distilled water in a $N_2$ atmosphere, a DMF solution of the compound (2, 1 g) was gradually added dropwise, and the solution was stirred for six hours at 60° C. The solution was then restored to room temperature, 2 mL of water was added, and the solution was filtered and dried, yielding a Bunte salt (3).

Dodecanethiol (0.41 g), methanol (2 mL), NaOH (0.088 g), and 1 mL of water were stirred for one hour in a $N_2$ atmosphere, a DMF solution of the Bunte salt was added, and the mixture was stirred for three hours. Water and ethyl acetate were added, the mixture was stirred, and the organic layer was collected. Separation by column chromatography was conducted using a mixed solvent of hexane and chloroform (1:3) as developing solvent, yielding the azobenzene derivative compound (4) of the present invention. The azobenzene derivative compound (4) was an orange crystal; the yield was 0.25 g.

$^1$H NMR (270 MHz, $CDCl_3$) δ 0.88 (t, 3H, $CH_3$), 1.2-1.6 (m, 34H, $CH_2$), 1.66 (m, 4H, $SSCH_2CH_2$), 1.83 (m, 2H, $ArOCH_2CH_2$), 2.68 (t, 4H, $SSCH_2$), 4.05 (t, 2H, $ArOCH_2$), 7.01 (d, 2H, J=8.91 Hz, Ar—H), 7.7-8.0 (m, 10H, Ar—H). FAB-MS (m/z): [M +H]+found, 700.3 (=M+1), calcd for $C_{43}H_{61}N_3OS_2$, 699.4. IR (ATR): 2920, 2850 (C—H stretching), 2240 (cyano group), 1603, 1584, 1499 (benzene ring), 1253 (Ph-O stretching), 1156 (=N-Ph stretching) $cm^{-1}$ A reaction schematic of the above synthesis method is given below:

Example 2

(1) Formation of Nanoparticles

The azobenzene derivative compound synthesized in Example 1 was dissolved in dichloromethane to a concentration of $4 \times 10^{-5}$ M. This solution was irradiated with UV light at a wavelength of 365 nm. Solutions that had been exposed to UV light for 120 minutes, 180 minutes, and 390 minutes were observed with scanning electron microscopy (SEM). The SEM images obtained are shown in FIG. 1.

Figure 1:
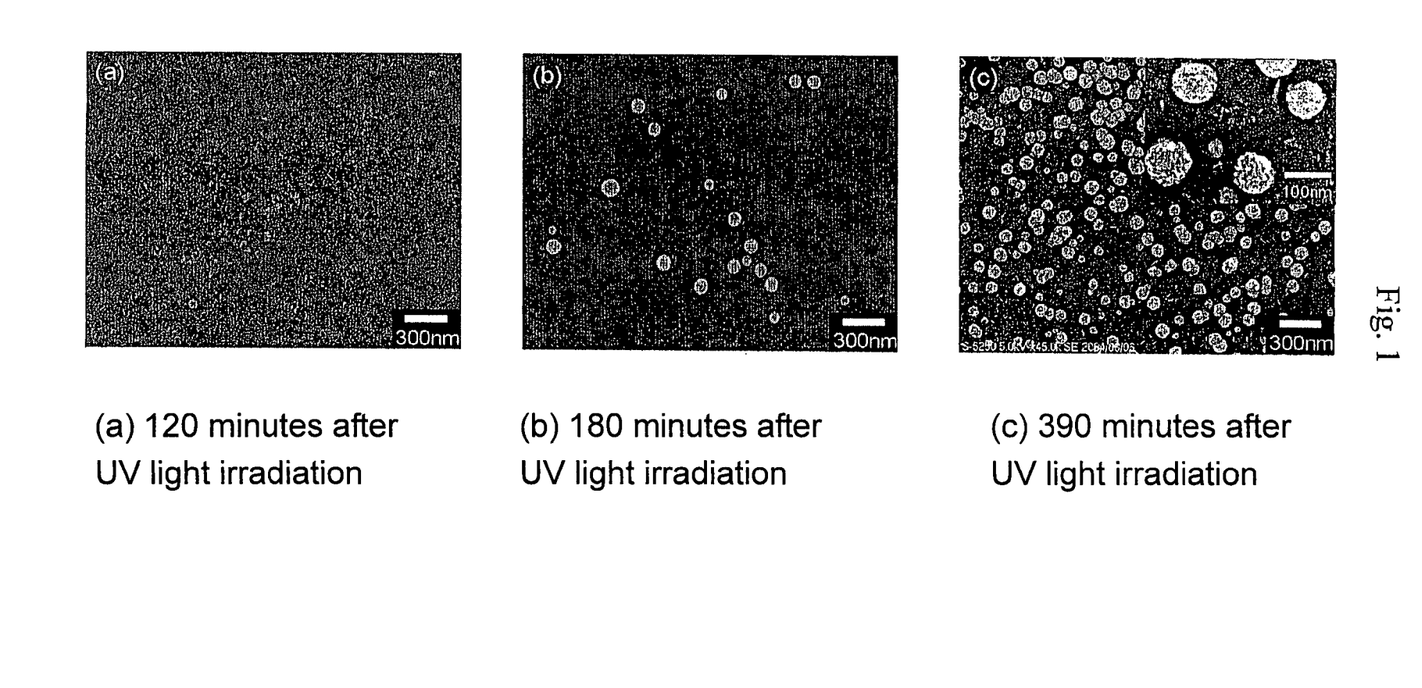
FIG. 1 shows SEM images obtained in Example 1.

From FIG. 1 it will be understood that irradiation with UV light of the solution containing the azobenzene derivative compound of the present invention resulted in the formation of aggregates (nanoparticles). The longer the exposure time of UV light, the greater the number of particles formed. The particles ranged in diameter from 10 to 150 nm.

From the above results, it is revealed that nanoparticles can be obtained from the azobenzene derivative compound of the present invention merely by irradiation with UV light.

Figure 2:
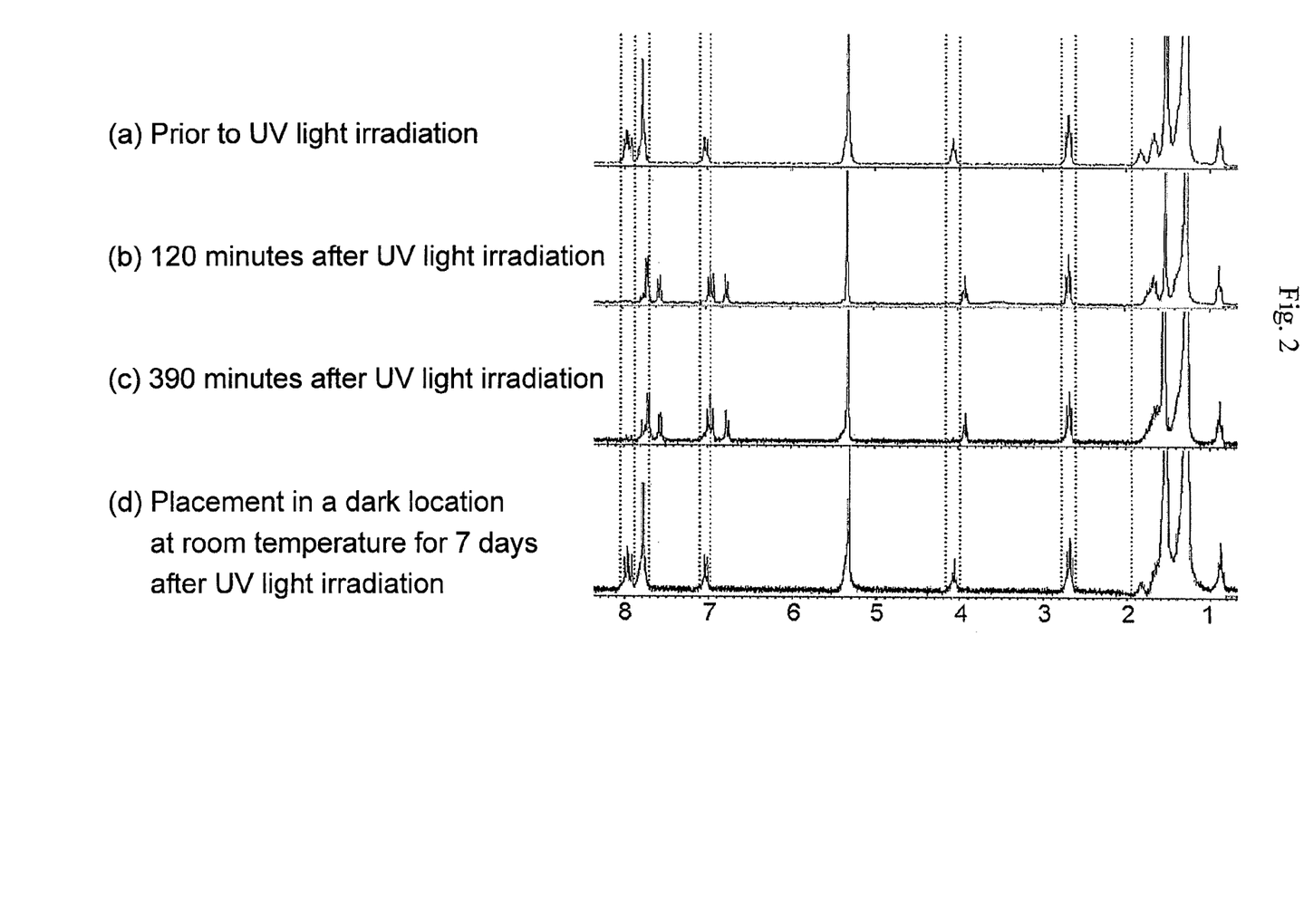
FIG. 2 shows NMR spectral changes due to irradiation with UV light.

FIG. 2 shows $^1$H-NMR spectra (solvent: $CD_2Cl_2$) for the individual solutions obtained in (1) above. In the NMR spectra, the peak in the vicinity of 7 to 8 ppm is derived from the phenyl of the azobenzene. Comparing the NMR spectra of FIGS. 2(a) and 2(b), the change in the shape of the peak near 7 to 8 ppm indicates isomerization from trans to cis form. In the NMR spectra of FIGS. 2(c) and 2(d), the change in the shape of the peak near 7 to 8 ppm reveals that the cis form changed back to the trans form when placed in a dark location at room temperature. Based on these comparisons, it will be understood that the azobenzene derivative compound of the present invention underwent good isomerization when irradiated with UV light and placed at room temperature; there was no problem in the form of a reduced isomerization rate.

On the other hand, the peak in the vicinity of 1 to 2 ppm is derived from the long-chain alkyl. In the NMR spectra of FIGS. 2(b) and 2(c), the change in the shape of the peak near 1 to 2 ppm was presumed to be the result of contribution by the alkyl moiety to aggregation of the azobenzene derivative compound of the present invention due to irradiation with UV light.

(2) Emission Enhancement by the Formation of Nanoparticles

Figure 3A:
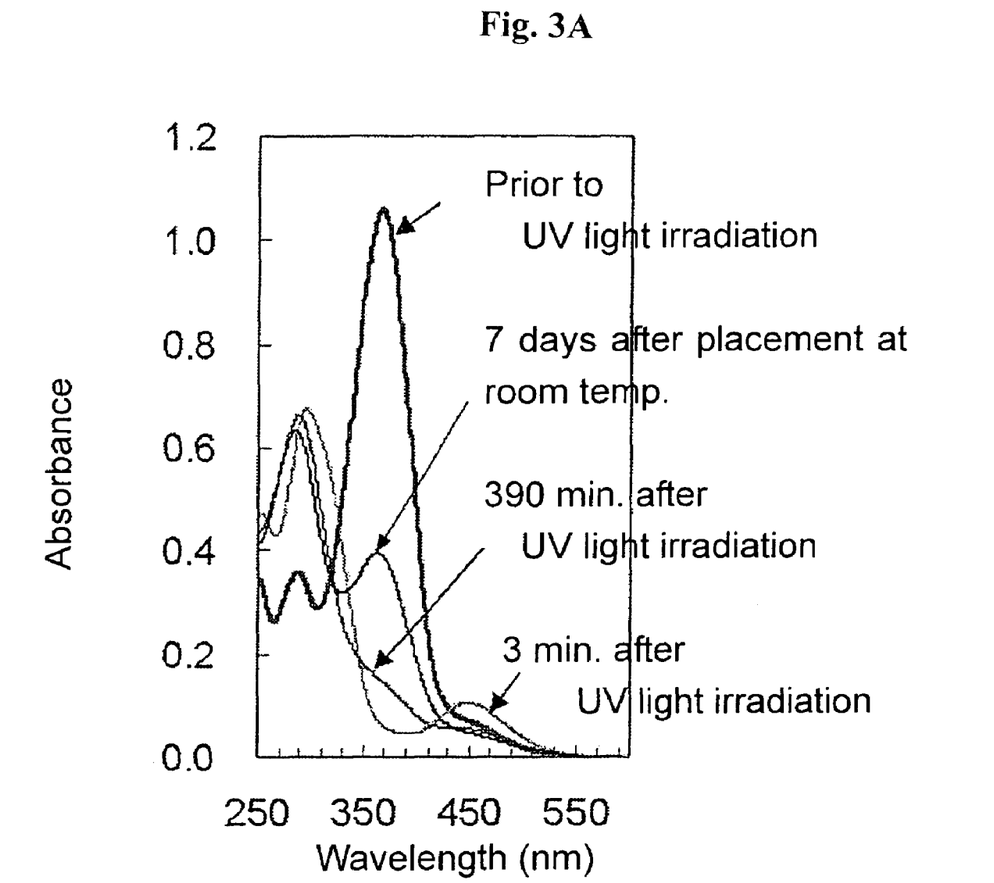
FIG. 3 shows changes in absorption spectra and fluorescent spectra due to irradiation with UV light.
Figure 3B:
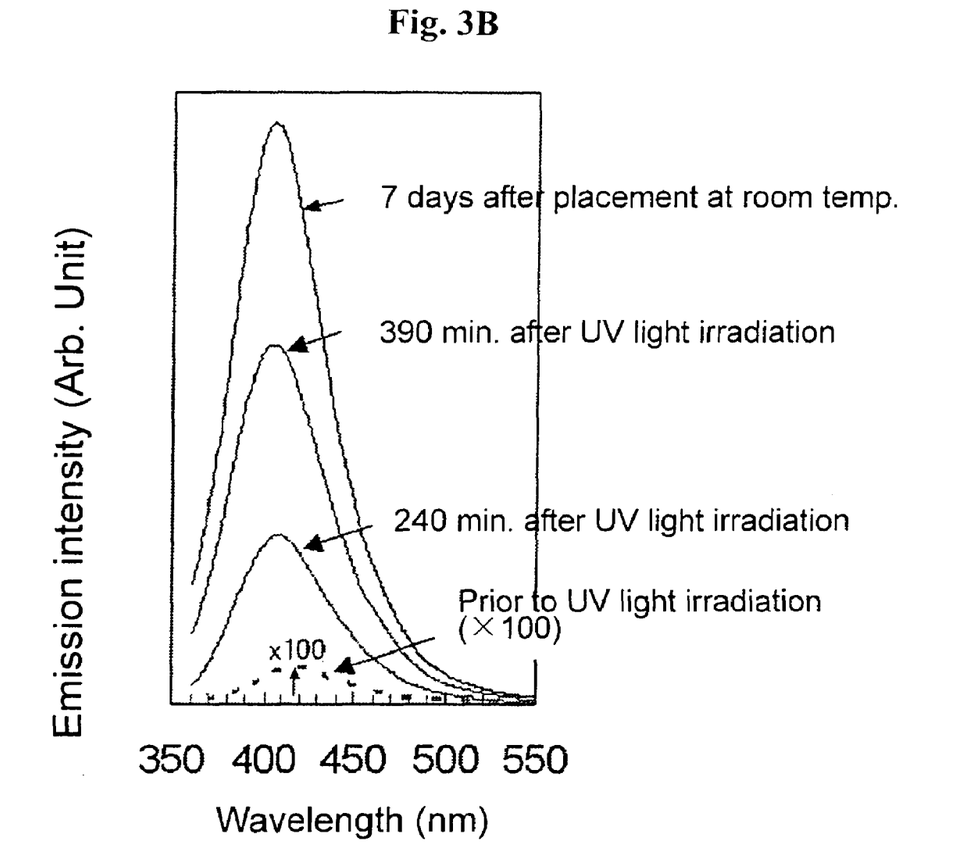
Figure 3C:
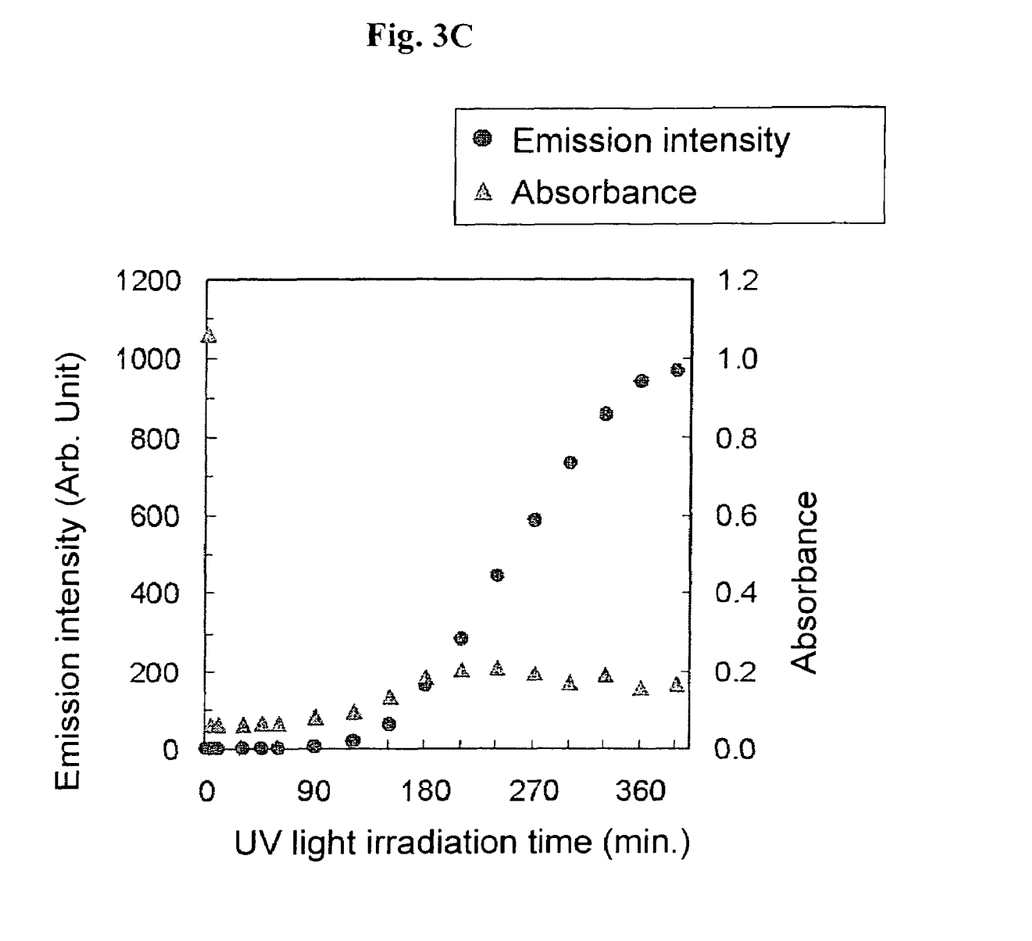

After irradiating a dichloromethane solution containing the azobenzene derivative compound with UV light (365 nm) for 390 minutes in the same manner as that set forth above, the solution was placed in a dark location at room temperature for seven days. FIG. 3(a) shows the absorption spectra of the solution prior to the start of irradiation with UV light, after three minutes of irradiation with UV light, after 390 minutes of irradiation with UV light, and after seven days at room temperature. Each of the solutions was irradiated with 325 nm excitation radiation at room temperature and fluorescence spectra were measured. FIG. 3(b) shows the emission spectra that were obtained. FIG. 3(c) shows changes over time in light emission intensity and absorbance. As shown in FIGS. 3(b) and (c), prior to irradiation with UV light, the azobenzene derivative compound indicated little fluorescence. Irradiation with UV light gradually increased the emission intensity. In the area following 120 minutes of irradiation with UV light, a particularly sharp increase was observed. After 390 minutes of irradiation with UV light, a light emission intensity of 1,000 times that prior to irradiation with UV light was exhibited. After standing for seven days at room temperature, the fluorescence intensity was enhanced to 1,600 times that prior to irradiation with UV light.

From the above results, it will be understood that when the azobenzene derivative compound of the present invention formed nanoparticles due to irradiation with UV light, it exhibited marked enhancement of emission.

From FIG. 3(a), it will be understood that the azobenzene derivative compound of the present invention had no problem in the form of a shift in the absorption band.

(3) Changes in Particle Diameter and Emission Wavelength Based on the Concentration of the Azobenzene Derivative Compound

Figure 4:
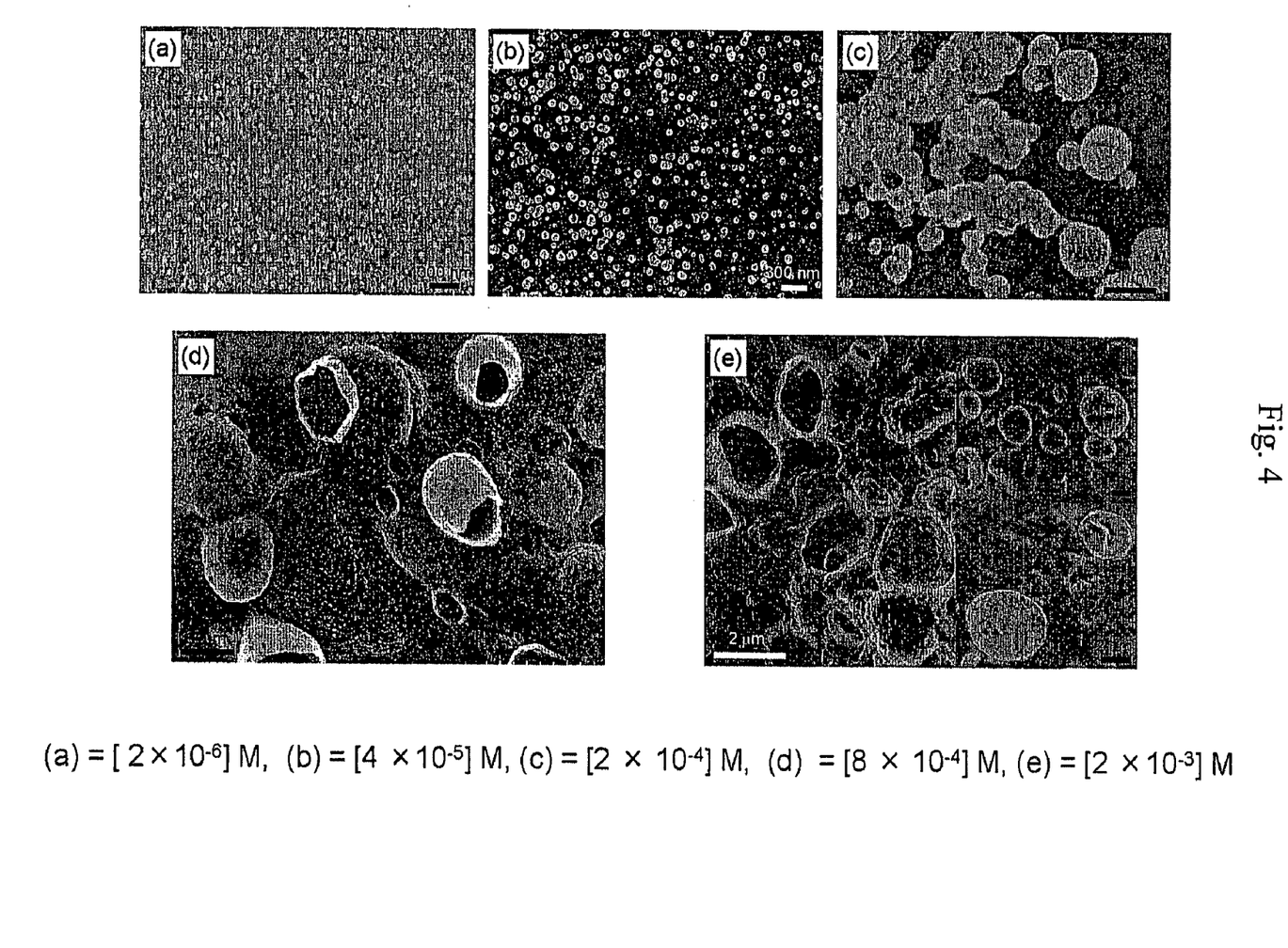
FIG. 4 shows SEM images obtained in Example 2.

The azobenzene derivative compound synthesized in Example 1 was dissolved at varying concentrations in dichloromethane and the solutions obtained were irradiated for 390 minutes with UV light (365 nm). The solutions were observed with scanning electron microscopy (SEM) following irradiation with UV light; the SEM images obtained are shown in FIG. 4. As revealed in FIG. 4, at an azobenzene derivative concentration of $2 \times 10^{-6}$ M, particles with a diameter of about 10 to 60 nm formed. At a concentration of $4 \times 10^{-5}$ M, particles with a diameter of about 10 to 150 nm formed. At a concentration of $2 \times 10^{-4}$ M, particles with a maximum diameter of about 3 μm formed. When the concentration was increased to $8 \times 10^{-4}$ M and $2 \times 10^{-3}$ M, particles with a maximum diameter of 10 μm formed. As mentioned above, it was possible to increase the concentration of the azobenzene derivative compound to form larger particles.

Figure 5:
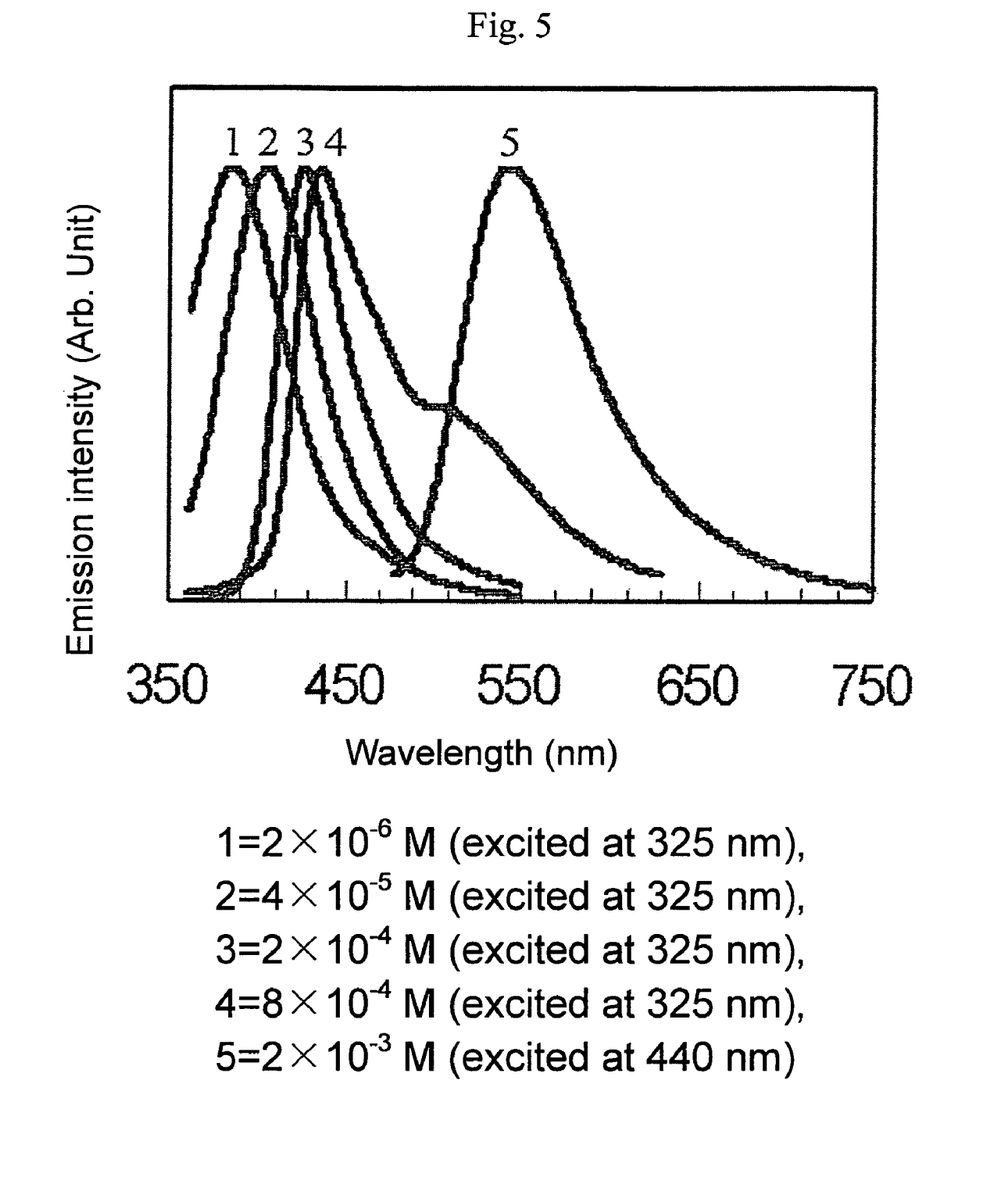
FIG. 5 shows changes in emission spectra based on the concentration of the azobenzene derivative compound.

Furthermore, FIG. 5 shows emission spectra obtained by irradiating each of the above solutions with excitation radiation. From FIG. 5, it will be understood that the lower the concentration of the azobenzene derivative compound, the greater the shift of the emission spectrum to the low wavelength side. This property can be utilized to obtain particles exhibiting fluorescence wavelengths suited to specific applications.

The azobenzene derivative compound of the present invention has no problem in the form of a shift in absorption band or a decreased isomerization rate, the aggregate (particle) formed by irradiation with UV light exhibits strong fluorescence, and storage at room temperature further enhances emission intensity. Application to light-emitting diodes (LEDs), fluorescent labels, optical sensors, and the like can be anticipated utilizing these characteristics of the azobenzene derivative compound and particle of the present invention.

The invention claimed is:

1. An azobenzene derivative compound denoted by general formula (I):

wherein $R_1$ denotes a halogen atom, amino group, ester group, nitro group, alkoxyl group, cycloalkyl group, or heterocyclic group; m and n each independently denote an integer ranging from 1 to 6; $R_2$ to $R_9$ each independently denote a hydrogen atom or alkyl group; p and q each independently denote an integer ranging from 3 to 28; and r is 1.

2. The azobenzene derivative compound according to claim 1, wherein, in general formula (I), $R_1$ denotes a, nitro group, alkoxyl group, or ester group.

3. The azobenzene derivative compound according to claim 1, wherein, in general formula (I), $R_1$ denotes a, heterocyclic group, or halogen atom.

4. The azobenzene derivative compound according to claim 1, wherein, in general formula (I), $R_2$ to $R_9$ all denote a hydrogen atom.

5. The azobenzene derivative compound according to claim 1, wherein, in general formula (I), n denotes an integer ranging from 2 to 6.

6. The azobenzene derivative compound according to claim 1, wherein, in general formula (I), m is 1 or 2.

7. The azobenzene derivative compound according to claim 1, wherein, in general formula (I), p and q each independently denote an integer ranging from 3 to 22.

8. A particle formed by aggregates of the azobenzene derivative compounds according to formula (I):

wherein $R_1$ denotes a halogen atom, amino group, ester group, nitro group, alkoxyl group, cycloalkyl group, or heterocyclic group; m and n each independently denote an integer ranging from 1 to 6; $R_2$ to $R_9$ each independently denote a hydrogen atom or alkyl group; p and g each independently denote an integer ranging from 3 to 28; and r denotes 0 or 1.

9. The particles of claim 8, wherein the particles have a diameter ranging from 10 nm to 10 μm.

10. A method of fabricating particles formed by aggregates of azobenzene derivative compounds denoted by general formula (I):

wherein $R_1$ denotes a hydrogen atom, halogen atom, cyano group, amino group, ester group, nitro group, alkyl group, alkoxyl group, cycloalkyl group, or heterocyclic group; m and n each independently denote an integer ranging from 1 to 6; $R_2$ to $R_9$ each independently denote a hydrogen atom or alkyl group; p and q each independently denote an integer ranging from 3 to 28; and r denotes 0 or 1,
   wherein UV light is irradiated to an organic solvent containing the azobenzene derivative compound to form aggregates of said azobenzene derivative compounds.

11. The method according to claim 10, wherein the concentration of said azobenzene derivative compound in the organic solvent ranges from $10^{-7}$ to $10^{-3}$ M.

12. The method according to claim 10, wherein the concentration of said azobenzene derivative compound in the organic solvent ranges from $10^{-6}$ to $10^{-4}$ M.

13. A method of fabricating particles formed by aggregates of azobenzene derivative compounds denoted by general formula (I):

wherein $R_1$ denotes a hydrogen atom, halogen atom, cyano group, amino group, ester group, nitro group, alkyl group, alkoxyl group, cycloalkyl group, or heterocyclic group; m and n each independently denote an integer ranging from 1 to 6; $R_2$ to $_9$ each independently denote a hydrogen atom or alkyl group; p and q each independently denote an integer ranging from 3 to 28; and r denotes 0 or 1,
   wherein the particles have a diameter ranging from 10 nm to 10 μm, and
   wherein UV light is irradiated to an organic solvent containing the azobenzene derivative compound to form aggregates of said azobenzene derivative compound.

14. The method according to claim 13, wherein the concentration of said azobenzene derivative compound in the organic solvent ranges from $10^{-7}$ to $10^{-3}$ M.

15. The method according to claim 13, wherein the concentration of said azobenzene derivative compound in the organic solvent ranges from $10^{-6}$ to $10^{-4}$ M.

* * * * *